(12) United States Patent
Sasaki et al.

(10) Patent No.: US 10,307,885 B2
(45) Date of Patent: Jun. 4, 2019

(54) METHOD FOR RAISING POLISHING PAD AND POLISHING METHOD

(71) Applicant: SHIN-ETSU HANDOTAI CO., LTD., Tokyo (JP)

(72) Inventors: Takuya Sasaki, Shirakawa (JP); Yuki Tanaka, Nishigo-mura (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 58 days.

(21) Appl. No.: 15/541,562

(22) PCT Filed: Jan. 5, 2016

(86) PCT No.: PCT/JP2016/000011
§ 371 (c)(1),
(2) Date: Jul. 5, 2017

(87) PCT Pub. No.: WO2016/125423
PCT Pub. Date: Aug. 11, 2016

(65) Prior Publication Data
US 2017/0341204 A1 Nov. 30, 2017

(30) Foreign Application Priority Data
Feb. 4, 2015 (JP) .................................. 2015-020606

(51) Int. Cl.
*B24B 37/08* (2012.01)
*B24B 37/24* (2012.01)
(Continued)

(52) U.S. Cl.
CPC ............ *B24B 53/017* (2013.01); *B24B 37/00* (2013.01); *B24B 37/08* (2013.01); *B24B 37/24* (2013.01);
(Continued)

(58) Field of Classification Search
CPC ......... B24B 37/08; B24B 37/24; B24B 49/12; B24B 49/18; B24B 53/017; B24B 53/02; G01N 23/223; G01N 2223/652; H01L 21/304; H01L 21/30625; H01L 21/67253
See application file for complete search history.

(56) References Cited

U.S. PATENT DOCUMENTS 6,306,025 B1   10/2001  Torii
7,070,479 B2 *  7/2006  Faustmann ............. B24B 49/02
                                                        451/21

(Continued)

FOREIGN PATENT DOCUMENTS

JP   H11-000868 A    1/1999
JP   2004-063482 A   2/2004
(Continued)

OTHER PUBLICATIONS

May 4, 2018 Taiwanese Office Action issued in Taiwanese Patent Application No. 105100464.
(Continued)

*Primary Examiner* — Timothy V Eley
(74) *Attorney, Agent, or Firm* — Oliff PLC

(57) ABSTRACT

A method for raising a polishing pad for polishing a silicon wafer, wherein a polishing pad made of foamed urethane resin is attached to a polishing machine, after dressing is performed, dummy polishing is performed, after processing to remove the polishing residues that have built up in the polishing pad by the dummy polishing is then performed, an amount of polishing residues in the polishing pad is measured, and a rise of the polishing pad subjected to the dummy polishing is judged based on the measured amount of polishing residues. As a result, a method for raising a polishing pad can improve the particle level in the polishing pad life early stage.

10 Claims, 4 Drawing Sheets

(51) Int. Cl.
*B24B 49/18* (2006.01)
*H01L 21/67* (2006.01)
*B24B 53/017* (2012.01)
*G01N 23/223* (2006.01)
*H01L 21/304* (2006.01)
*H01L 21/306* (2006.01)
*B24B 37/00* (2012.01)
*H01L 21/02* (2006.01)

(52) U.S. Cl.
CPC ........... *B24B 49/18* (2013.01); *G01N 23/223* (2013.01); *H01L 21/02057* (2013.01); *H01L 21/304* (2013.01); *H01L 21/30625* (2013.01); *H01L 21/67253* (2013.01); *G01N 2223/6116* (2013.01); *G01N 2223/652* (2013.01)

(56) References Cited

U.S. PATENT DOCUMENTS

| | | | |
|---|---|---|---|
| 7,359,069 B2 * | 4/2008 | Tanaka | ............... B24B 37/26 356/630 |
| 8,221,193 B2 * | 7/2012 | Chang | ............... B24B 37/042 451/5 |
| 2003/0013389 A1 | 1/2003 | Hollatz et al. | |
| 2005/0221720 A1 | 10/2005 | Ono | |
| 2011/0070745 A1 | 3/2011 | Matsui et al. | |

FOREIGN PATENT DOCUMENTS

| | | |
|---|---|---|
| JP | 2005-209863 A | 8/2005 |
| JP | 2005-288664 A | 10/2005 |
| JP | 2006-332550 A | 12/2006 |
| JP | 2011-071215 A | 4/2011 |
| TW | I272672 B | 2/2007 |

OTHER PUBLICATIONS

Apr. 5, 2016 International Search report issued in International Patent Application No. PCT/JP2016/000011.

Nov. 30, 2018 Office Action issued in Taiwanese Patent Application No. 105100464.

* cited by examiner

METHOD FOR RAISING POLISHING PAD AND POLISHING METHOD

TECHNICAL FIELD

The present invention relates to a method for raising a polishing pad for polishing a silicon wafer and a method for polishing a silicon wafer by using the polishing pad.

BACKGROUND ART

In general, in a wafer polishing process, in polishing which is performed immediately after attachment of a polishing pad to a polishing machine, generation of a scratch on a wafer or significant degradation of the particle level is sometimes observed. Furthermore, the larger the polishing machine becomes, the more likely the generation of a scratch or degradation of the particle level is to occur. It is considered that the generation of a scratch and degradation of the particle level occur due to an insufficient rise of the just-attached polishing pad.

In raising the polishing pad, dressing is generally performed by using a dresser or the like with a surface covered with diamonds as described in Patent Document 1 in order to adjust the surface roughness or thickness of the polishing pad. However, even when the polishing pad is raised by such dressing, degradation of the particle level is observed immediately after the start of polishing (hereinafter also referred to as the "polishing pad life early stage"), which makes it clear that dressing alone results in an insufficient rise of the polishing pad.

CITATION LIST

Patent Document

Patent Document 1: Japanese Unexamined Patent publication (Kokai) No. H11-000868

SUMMARY OF INVENTION

Technical Problem

The present invention has been made to solve the problem, and an object thereof is to provide a method for raising a polishing pad that can improve the particle level in the polishing pad life early stage. Moreover, another object of the present invention is to provide a polishing method that can improve the particle level in the polishing pad life early stage.

Solution to Problem

To attain the object, the present invention provides a method for raising a polishing pad for polishing a silicon wafer, wherein a polishing pad made of foamed urethane resin is attached to a polishing machine, after dressing is performed, dummy polishing is performed, after processing to remove polishing residues that have built up in the polishing pad by the dummy polishing is then performed, the amount of polishing residues in the polishing pad is measured, and a rise of the polishing pad subjected to the dummy polishing is judged based on the measured amount of polishing residues.

With such a raising method, the polishing pad is raised by dummy polishing in addition to dressing and a judgment as to whether or not the polishing pad after the dummy polishing has sufficiently risen is made, which makes it possible to raise the polishing pad until the polishing pad sufficiently rises and thereby improve the particle level in the polishing pad life early stage.

Moreover, it is preferable that the judgment is made as follows: by performing polishing of a silicon wafer by using a reference polishing pad made of foamed urethane resin separately subjected only to dressing, processing to remove polishing residues which is performed by the same means as that used in the removal processing after the dummy polishing, and measurement of an amount of polishing residues after the removal processing, the amount of polishing residues in the reference polishing pad at a point in time at which a value of (an amount of time the reference polishing pad was used)/(a previously set life of the reference polishing pad) is 0.05 is determined as a reference value in advance, and, if the amount of polishing residues measured after the dummy polishing and the removal processing is greater than or equal to the reference value, a judgment is made that the polishing pad subjected to the dummy polishing has risen.

Since such a method makes it possible to make a more reliable judgment as to whether or not the polishing pad after the dummy polishing has sufficiently risen, it is possible to improve the particle level in the polishing pad life early stage more reliably.

Furthermore, at this time, it is preferable that the amount of polishing residues is measured by detecting a signal containing a Si—Kα ray from a fluorescent X-ray spectrum which is obtained by a fluorescent X-ray analysis method.

Such a method makes it possible to measure the amount of polishing residues with ease.

Moreover, at this time, it is preferable that the processing to remove polishing residues is performed by dressing and high-pressure jet water cleaning.

Such a method makes it possible to perform the processing to remove polishing residues with ease.

Furthermore, at this time, the polishing machine may be a double-side polishing machine, for example.

As described above, the method for raising a polishing pad of the present invention can also be applied to a case in which a double-side polishing machine is used.

In addition, the present invention provides a method for polishing a silicon wafer by using a polishing pad, wherein a polishing pad made of foamed urethane resin is attached to a polishing machine, after dressing is performed, dummy polishing is performed, after processing to remove polishing residues that have built up in the polishing pad by the dummy polishing is then performed, an amount of polishing residues in the polishing pad is measured, a polishing pad that is used in polishing of the silicon wafer is selected based on the measured amount of polishing residues, and polishing of the silicon wafer is performed by using the selected polishing pad.

With such a polishing method, since a polishing pad is raised by dummy polishing in addition to dressing and a polishing pad that has sufficiently risen by the dummy polishing is selected and used in polishing, it is possible to improve the particle level in the polishing pad life early stage.

Moreover, it is preferable that the selection is made as follows: by performing polishing of a silicon wafer by using a reference polishing pad made of foamed urethane resin separately subjected only to dressing, processing to remove polishing residues which is performed by the same means as that used in the removal processing after the dummy polishing, and measurement of an amount of polishing residues after the removal processing, the amount of polishing residues in the reference polishing pad at a point in time at which a value of (an amount of time the reference polishing pad was used)/(a previously set life of the reference polishing pad) is 0.05 is determined as a reference value in advance, and a polishing pad whose amount of polishing residues measured after the dummy polishing and the removal processing is greater than or equal to the reference value is selected as a polishing pad that is used in polishing of the silicon wafer.

Since such a method makes it possible to select more reliably a polishing pad that has sufficiently risen, it is possible to improve the particle level in the polishing pad life early stage more reliably.

Furthermore, at this time, it is preferable that the amount of polishing residues is measured by detecting a signal containing a Si—Kα ray from a fluorescent X-ray spectrum which is obtained by a fluorescent X-ray analysis method.

Such a method makes it possible to measure the amount of polishing residues with ease.

Moreover, at this time, it is preferable that the processing to remove polishing residues is performed by dressing and high-pressure jet water cleaning.

Such a method makes it possible to perform processing to remove polishing residues with ease.

Furthermore, at this time, the polishing machine may be a double-side polishing machine, for example.

As described above, the polishing method of the present invention can also be applied to a case in which a double-side polishing machine is used.

Advantageous Effects of Invention

As described above, with the method for raising a polishing pad of the present invention, a polishing pad is raised by dummy polishing in addition to conventional dressing and a judgment is made as to whether or not the polishing pad after the dummy polishing has sufficiently risen to such an extent that generation of a scratch or degradation of particles is not observed, which makes it possible to raise the polishing pad until the polishing pad sufficiently rises and thereby improve the particle level in the polishing pad life early stage. Moreover, since the dummy polishing can be finished at a point in time at which the polishing pad is judged to have risen, the dummy polishing is not performed for an unnecessary long time, which makes it possible to raise the polishing pad efficiently.

Furthermore, with the polishing method of the present invention, since a polishing pad is raised by dummy polishing in addition to dressing and a polishing pad that has sufficiently risen by the dummy polishing to such an extent that generation of a scratch or degradation of particles is not observed is selected and used in polishing, it is possible to improve the particle level in the polishing pad life early stage.

DESCRIPTION OF EMBODIMENTS

As described above, it has become clear that, since conventional raising by dressing (hereinafter also referred to as the "conventional method") results in an insufficient rise of a polishing pad, if main polishing (polishing of a product wafer) is performed by using the polishing pad subjected to raising by such a conventional method, the particle level degrades in the polishing pad life early stage.

Figure 6:
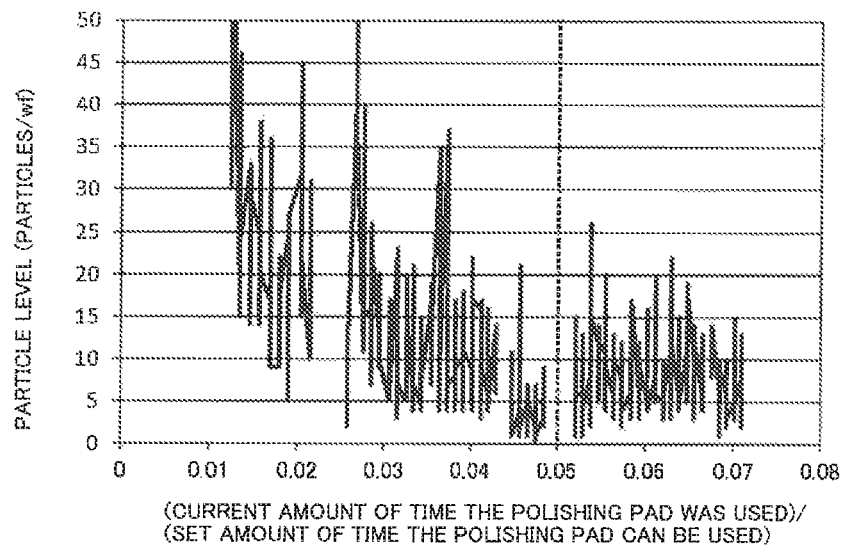
FIG. 6 is a graph showing the particle level in each amount of time the polishing pad was used in Comparative Example 1 (a case in which main polishing is performed after raising by the conventional method)

Here, the particle level in each amount of time the polishing pad was used which is observed when main polishing is performed after raising by the conventional method is shown in FIG. 6. As shown in FIG. 6, it is clear that, when raising is performed by the conventional method, the particle level degrades in the polishing pad life early stage, in particular, until a point in time at which the value of (the current amount of time the polishing pad was used)/(the set amount of time the polishing pad can be used) becomes 0.05.

The inventors of the present invention have conducted an intensive study to improve the particle level in the polishing pad life early stage and focused attention on the amount of polishing residues in a polishing pad and a rise of the polishing pad. As a result of the study conducted by the inventors of the present invention, the inventors have found out that, in a polishing pad that has sufficiently risen to such an extent that degradation of the particle level is not observed, more polishing residues have built up in the polishing pad than those in the polishing pad life early stage, which makes it possible to judge the state of a rise of the polishing pad based on the amount of polishing residues in the polishing pad. In addition, as a result of a series of intensive studies, the inventors of the present invention have found out that it is possible to improve the particle level in the polishing pad life early stage by raising a polishing pad through performing dummy polishing to make polishing residues build up in the polishing pad, judging a rise based on the amount of polishing residues after the dummy polishing, and performing main polishing by using a polishing pad that is judged to have sufficiently risen, and made the present invention.

That is, the present invention is a method for raising a polishing pad for polishing a silicon wafer, wherein a polishing pad made of foamed urethane resin is attached to a polishing machine, after dressing is performed, dummy polishing is performed, after processing to remove the polishing residues that have built up in the polishing pad by the dummy polishing is then performed, an amount of polishing residues in the polishing pad is measured, and a rise of the polishing pad subjected to the dummy polishing is judged based on the measured amount of polishing residues.

Hereinafter, the present invention will be described in detail, but the present invention is not limited to the following description.

Incidentally, in the present invention, the value of (the current amount of time the polishing pad was used)/(the set amount of time the polishing pad can be used) becoming equal to 1 means that the polishing pad has to be replaced with another polishing pad, and a point in time at which the value of (the current amount of time the polishing pad was used)/(the set amount of time the polishing pad can be used) is 0.05 means a point in time at which 5% of the previously set life of the polishing pad was used.

<Method for Raising a Polishing Pad>

Hereinafter, the method for raising a polishing pad of the present invention will be described in detail with reference to the drawings.

Figure 1:
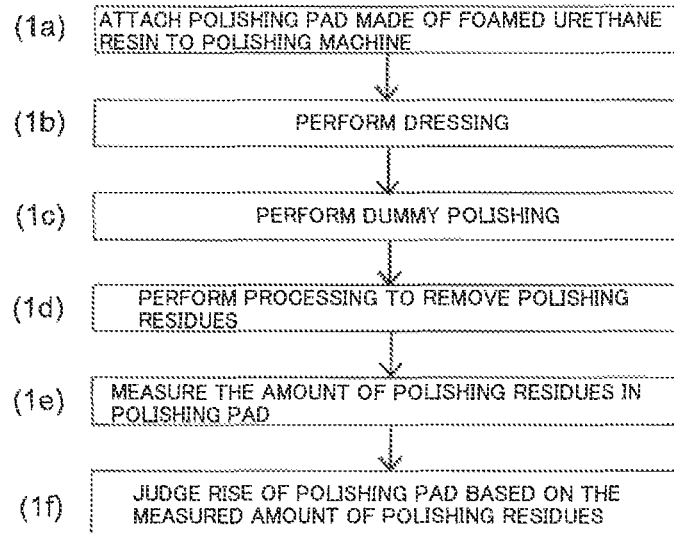
FIG. 1 is a flow diagram showing an example of a method for raising a polishing pad of the present invention.

FIG. 1 is a flow diagram showing an example of the method for raising a polishing pad of the present invention. In the method for raising a polishing pad of the present invention, a polishing pad made of foamed urethane resin is first attached to a polishing machine (FIG. 1(1a)), after dressing is performed (FIG. 1(1b)), dummy polishing is performed (FIG. 1(1c)), after processing to remove the polishing residues that have built up in the polishing pad by the dummy polishing is then performed (FIG. 1(1d)), an amount of polishing residues in the polishing pad is measured (FIG. 1(1e)), and a rise of the polishing pad subjected to the dummy polishing is judged based on the measured amount of polishing residues (FIG. 1(1f)).

Hereinafter, each process will be described in more detail.

First, a polishing pad made of foamed urethane resin is attached to a polishing machine (FIG. 1(1a)). At this time, the polishing machine is not limited to a particular polishing machine; for example, a double-side polishing machine or the like can be suitably used. Moreover, the method for raising a polishing pad of the present invention can be applied irrespective of the size of the polishing machine.

Next, dressing is performed (FIG. 1(1b)). The dressing method is not limited to a particular method; for instance, a dresser or the like with a surface covered with diamonds which is usually used in raising a polishing pad can be suitably used.

Next, dummy polishing is performed (FIG. 1(1c)). In general, when polishing of a wafer is performed, during intervals between polishing operations, processing to remove the polishing residues that have built up in the polishing pad (for example, processing (dressing) to grind the polishing pad by using a dresser covered with diamonds, processing (high-pressure jet water cleaning) to perform cleaning by spraying high-pressure jet water on the polishing pad, and so forth) is performed. As a result of this removal processing being performed, most of the polishing residues that have built up in the polishing pad are removed, but some of the polishing residues remain in the polishing pad even after the removal processing and raise the polishing pad. Thus, in the method for raising a polishing pad of the present invention, dummy polishing is performed after dressing to intentionally make polishing residues build up in the polishing pad and thereby raise the polishing pad.

For dummy polishing, although no particular limitation is imposed, a silicon wafer or the like which is commonly used in dummy polishing can be suitably used. Moreover, a polishing agent is not limited to a particular polishing agent and a colloidal silica polishing agent or the like can be suitably used.

Figure 7:
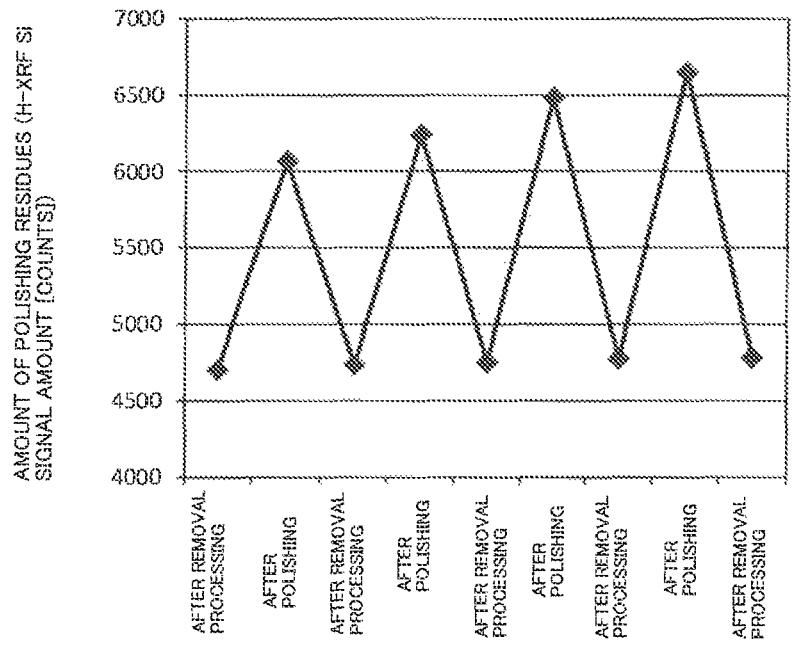
FIG. 7 is a graph showing changes in the amount of polishing residues when wafer polishing and processing to remove polishing residues are alternately repeated.

Here, in FIG. 7, changes in the amount of polishing residues when wafer polishing and processing to remove the polishing residues are alternately repeated are shown. Incidentally, a polishing stock removal per polishing operation in this case was set at 15 μm. As shown in FIG. 7, when wafer polishing and processing to remove the polishing residues are alternately performed, since most of the polishing residues that have built up by the polishing are removed by the removal processing in each time, the amount of polishing residues after the removal processing is less likely to increase. Therefore, in order to increase the amount of polishing residues after removal processing efficiently, it is preferable to perform dummy polishing in a row without performing removal processing in such a way as to achieve a polishing stock removal to be obtained by multiple operations of normal polishing (a polishing stock removal: about 10 to 20 μm). More specifically, it is preferable to perform dummy polishing in a row in such a way as to achieve a polishing stock removal of about 30 to 150 μm, more preferably, about 50 to 100 μm.

Next, processing to remove the polishing residues that have built up in the polishing pad by the dummy polishing is performed (FIG. 1(1d)). The method of processing to remove the polishing residues is not limited to a particular method; for example, it is preferable to perform the processing by dressing and high-pressure jet water cleaning. Incidentally, a dresser or the like with a surface covered with diamonds can be suitably used in dressing, as the dressing performed before the dummy polishing mentioned above. Such a method makes it possible to perform processing to remove the polishing residues with ease.

Next, the amount of polishing residues in the polishing pad is measured (FIG. 1(1e)). Incidentally, the amount of polishing residues which is measured here is the amount of polishing residues remaining in the polishing pad after the removal processing. The method for measuring the amount of polishing residues is not limited to a particular method; for example, it is preferable to measure the amount of polishing residues by detecting a signal containing a Si—Kα ray from a fluorescent X-ray spectrum which is obtained by a fluorescent X-ray analysis method.

When the amount of polishing residues is measured by the fluorescent X-ray analysis method, the amount of polishing residues can be specifically measured by the following method. When a silicon wafer is polished, since the polishing residues that have built up in the polishing pad contain Si elements, by detecting a signal containing a Si—Kα ray from a fluorescent X-ray spectrum, it is possible to measure the amount of polishing residues. More specifically, a value which is determined by integrating the signal amounts in the 1.6 to 1.9 eV range containing a Si—Kα ray from the detected fluorescent X-ray spectrum can be used as an standard value of the amount of polishing residues (hereinafter, this standard value is referred to as a "Si signal amount").

For measurement of the Si signal amount, MESA-630 manufactured by HORIBA, Ltd., for example, can be used; a measurement recipe in this case is preferably, for example, in Alloy LE FP, an X-ray irradiation time of 60 seconds. By measuring the Si signal amount of the polishing pad subjected to dummy polishing by using such an apparatus and regarding this Si signal amount as the amount of polishing residues, it is possible to measure the amount of polishing residues with ease.

Next, a rise of the polishing pad subjected to the dummy polishing is judged based on the measured amount of polishing residues (FIG. 1(1f)). At this time, it is preferable that a judgment is made as follows: by performing polishing of a silicon wafer by using a reference polishing pad made of foamed urethane resin separately subjected only to dressing, processing to remove the polishing residues which is performed by the same means as that used in the removal processing after the dummy polishing, and measurement of the amount of polishing residues after the removal processing, the amount of polishing residues in the reference polishing pad at a point in time at which a value of (an amount of time the reference polishing pad was used)/(a previously set life of the reference polishing pad) is 0.05 is determined as a reference value in advance, and, if the amount of polishing residues measured after the dummy polishing and the removal processing is greater than or equal to the reference value, a judgment is made that the polishing pad subjected to the dummy polishing has risen. It goes without saying that the judgment method is not limited to that described above.

Hereinafter, the judgment method will be described in more detail.

The study conducted by the inventors of the present invention has revealed that, as described above, when main polishing is performed by using a polishing pad raised by the conventional method, although the particle level degrades until a point in time at which the value of (the current amount of time the polishing pad was used)/(the set amount of time the polishing pad can be used) is 0.05, after the value of (the current amount of time the polishing pad was used)/(the set amount of time the polishing pad can be used) becomes 0.05 or greater, degradation of the particle level is suppressed (refer to FIG. 6). Based on the above findings, in the above-mentioned judgment method, on the assumption that the polishing pad has sufficiently risen at a point in time at which the value of (the current amount of time the polishing pad was used)/(the set amount of time the polishing pad can be used) is 0.05, a judgment regarding a rise is made with reference to the amount of polishing residues in the polishing pad at this point in time.

Specifically, a reference value which is used as a criterion of judgment is determined. More specifically, after performing polishing of a silicon wafer by using a polishing pad (a reference polishing pad) made of foamed urethane resin separately subjected only to dressing (raising by the conventional method) and then performing processing to remove the polishing residues, measurement of the amount of polishing residues is performed, and the amount of polishing residues in the reference polishing pad at a point in time at which the value of (the current amount of time the polishing pad was used)/(the set amount of time the polishing pad can be used) is 0.05 is determined as a reference value. Incidentally, at this time, the processing to remove the polishing residues is performed by the same means as that in the removal processing after the dummy polishing.

Next, a judgment is actually made. More specifically, the amount of polishing residues (that is, the amount of polishing residues in the polishing pad subjected to the dummy polishing) measured after the dummy polishing and the removal processing performed in the manner described above is compared with the reference value determined in the above-mentioned manner, and, if the amount of polishing residues in the polishing pad subjected to the dummy polishing is greater than or equal to the reference value, a judgment is made that the polishing pad subjected to the dummy polishing has risen.

Figure 8:
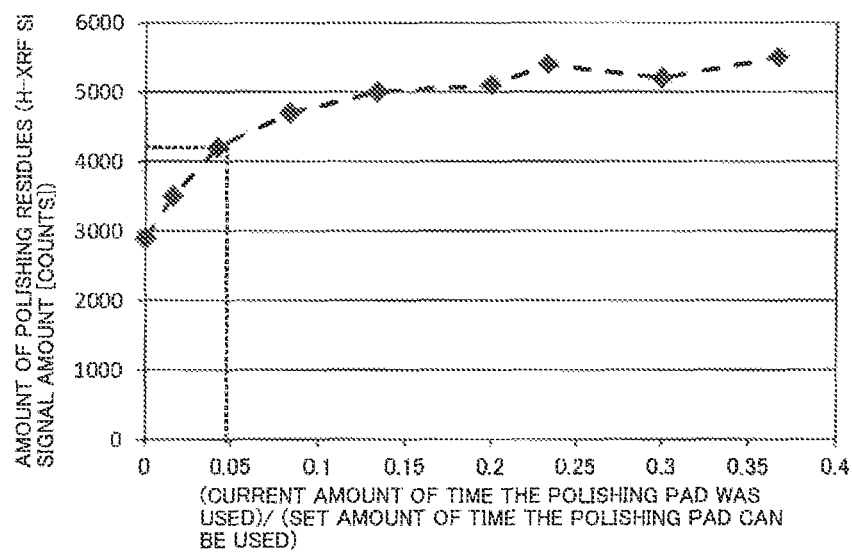
FIG. 8 is a graph showing the amount of polishing residues in each amount of time the polishing pad was used when main polishing is performed after raising by the conventional method.

Here, the amount of polishing residues in each amount of time the polishing pad was used when main polishing is actually performed after raising by the conventional method is shown in FIG. 8. Incidentally, the amount of polishing residues which is described here is a value measured after the processing to remove the polishing residues. The reference value in the judgment method is, for example, a value (about 4200) indicated by a dotted line in FIG. 8.

Since such a judgment method makes it possible to make a more reliable judgment as to whether or not the polishing pad after the dummy polishing has sufficiently risen, it is possible to improve the particle level in the polishing pad life early stage more reliably. Moreover, since an accurate judgment regarding a rise can be made, there is no need to perform additional dummy polishing. This makes it possible to reduce a waste of time or costs caused by unnecessary dummy polishing and perform raising efficiently.

Incidentally, if a rise is judged to be insufficient by the judgment regarding a rise, the dummy polishing (FIG. 1(1c)), the processing to remove the polishing residues (FIG. 1(1d)), the measurement of the amount of polishing residues (FIG. 1(1e)), and the judgment regarding a rise (FIG. 1(1f)) may be repeated until a judgment is made that the polishing pad has risen.

As described above, with the method for raising a polishing pad of the present invention, the polishing pad is raised by dummy polishing in addition to conventional dressing and a judgment is made as to whether or not the polishing pad after the dummy polishing has sufficiently risen to such an extent that generation of a scratch or degradation of particles is not observed, which makes it possible to raise the polishing pad until the polishing pad sufficiently rises and thereby improve the particle level in the polishing pad life early stage efficiently.

<Polishing Method>

Moreover, the present invention provides a method for polishing a silicon wafer by using a polishing pad, wherein a polishing pad made of foamed urethane resin is attached to a polishing machine, after dressing is performed, dummy polishing is performed, after processing to remove the polishing residues that have built up in the polishing pad by the dummy polishing is then performed, an amount of polishing residues in the polishing pad is measured, a polishing pad that is used in polishing of the silicon wafer is selected based on the measured amount of polishing residues, and polishing of the silicon wafer is performed by using the selected polishing pad.

Hereinafter, the polishing method of the present invention will be specifically described with reference to the drawing.

Figure 2:
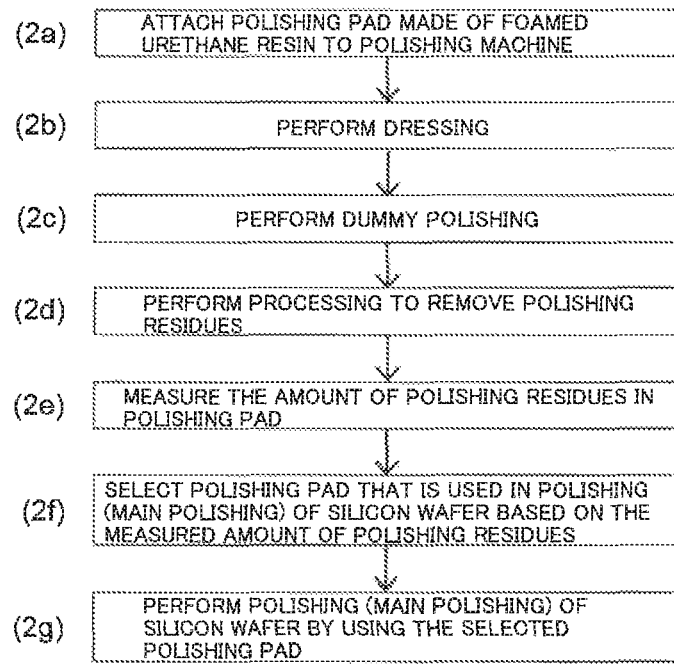
FIG. 2 is a flow diagram showing an example of a polishing method of the present invention.

FIG. 2 is a flow diagram showing an example of the polishing method of the present invention. In the polishing method of the present invention, a polishing pad made of foamed urethane resin is first attached to a polishing machine (FIG. 2(2a)), after dressing is performed (FIG. 2(2b)), dummy polishing is performed (FIG. 2(2c)), after processing to remove the polishing residues that have built up in the polishing pad by the dummy polishing is then performed (FIG. 2(2d)), the amount of polishing residues in the polishing pad is measured (FIG. 2(2e)), a polishing pad that is used in polishing of a silicon wafer is selected based on the measured amount of polishing residues (FIG. 2(2f)), and polishing of the silicon wafer is performed by using the selected polishing pad (FIG. 2(2g)).

Hereinafter, each processing will be described in more detail.

First, a polishing pad made of foamed urethane resin is attached to a polishing machine (FIG. 2(2a)). As the polishing machine, the same polishing machine as that mentioned in the method for raising a polishing pad of the present invention can be used.

Next, dressing is performed (FIG. 2(2b)). The dressing can be performed in the same manner as the dressing in the method for raising a polishing pad of the present invention.

Next, dummy polishing is performed (FIG. 2(2c)). The dummy polishing can be performed in the same manner as the dummy polishing in the method for raising a polishing pad of the present invention.

Next, processing to remove the polishing residues that have built up in the polishing pad by the dummy polishing is performed (FIG. 2(2d)). The processing to remove the polishing residues can be performed in the same manner as the processing to remove the polishing residues in the method for raising a polishing pad of the present invention.

Next, the amount of polishing residues in the polishing pad is measured (FIG. 2(2e)). The measurement of the amount of polishing residues can be performed in the same manner as the measurement of the amount of polishing residues in the method for raising a polishing pad of the present invention.

Next, a polishing pad that is used in polishing of a silicon wafer is selected based on the measured amount of polishing residues (FIG. 2(2f)). The selection can be made in the same manner as the judgment regarding a rise of the polishing pad in the method for raising a polishing pad of the present invention. Specifically, a polishing pad judged to have risen in the judgment can be selected as a polishing pad that is used in polishing of a silicon wafer.

Moreover, to the polishing pad that has not been selected, the dummy polishing (FIG. 2(2c)), the processing to remove the polishing residues (FIG. 2(2d)), the measurement of the amount of polishing residues (FIG. 2(2e)), and the selection (FIG. 2(2f)) may be repeated until the polishing pad is selected.

Next, polishing of the silicon wafer is performed by using the selected polishing pad (FIG. 2(2g)). As a polishing agent, for example, the same polishing agent as that mentioned in the dummy polishing in the method for raising a polishing pad of the present invention can be used.

As described above, with the polishing method of the present invention, since a polishing pad is raised by dummy polishing in addition to dressing and a polishing pad that has sufficiently risen by the dummy polishing to such an extent that generation of a scratch or degradation of particles is not observed is selected and used in polishing, it is possible to improve the particle level in the polishing pad life early stage.

EXAMPLES

Hereinafter, the present invention will be described specifically with Example and Comparative Example, but the present invention is not limited to these examples.

Incidentally, in Example and Comparative Example, for measurement of the amount of polishing residues, MESA-630 manufactured by HORIBA, Ltd. was used, and a measurement recipe was, in Alloy LE FP, an X-ray irradiation time of 60 seconds.

Comparative Example 1

Figure 4:
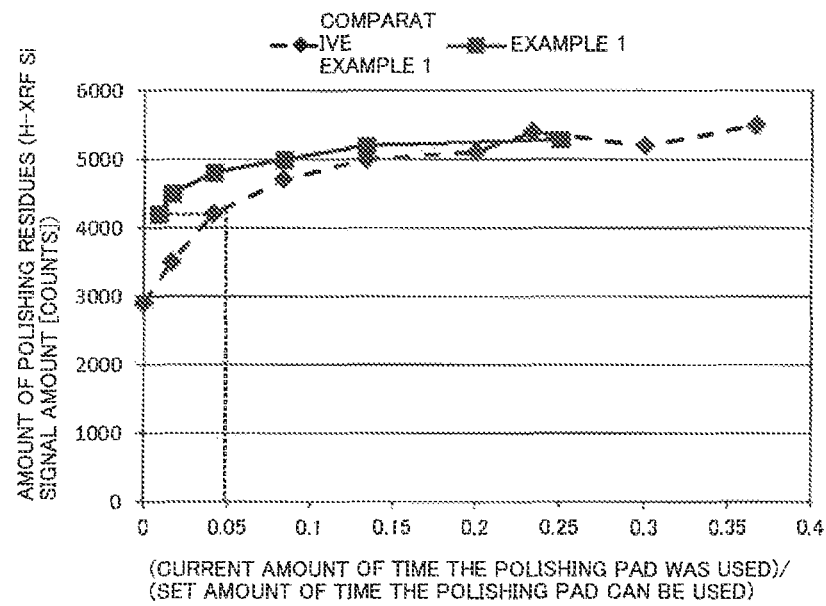
FIG. 4 is a graph showing the amount of polishing residues in each amount of time the polishing pad was used in Example 1 and Comparative Example 1.

A polishing pad made of foamed urethane resin was attached to a polishing machine, after dressing of the polishing pad was performed by using a dresser with a surface covered with diamonds, polishing (main polishing) of a wafer was performed under the following main polishing conditions without performing dummy polishing, and the amount of polishing residues and the particle level in each amount of time the polishing pad was used were measured. The amount of polishing residues in each amount of time the polishing pad was used is shown in FIG. 4. Moreover, the particle level in each amount of time the polishing pad was used is shown in FIG. 6. Furthermore, at this time, the amount of polishing residues at a point in time at which the value of (the current amount of time the polishing pad was used)/(the set amount of time the polishing pad can be used) was 0.05 was determined as a reference value.

(Main Polishing Conditions)

Polishing machine used: a 30B double-side polishing machine

Sample wafer: CZ, P-type, crystal orientation <100>, a diameter of 300 mm, a silicon wafer Polishing pad: a polishing pad made of foamed urethane resin Polishing agent: a colloidal silica polishing agent Polishing load: 180 g/cm$^2$ Polishing stock removal: 15 µm Example 1

Figure 3:
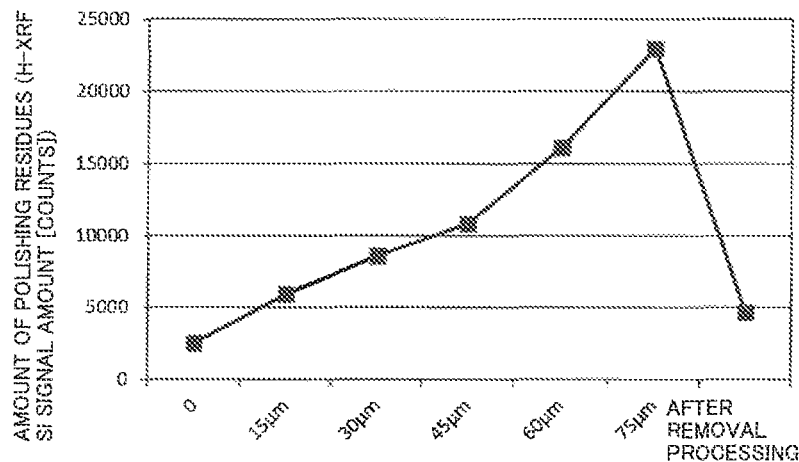
FIG. 3 is a graph showing the amount of polishing residues measured every time 15-µm dummy polishing was performed and the amount of polishing residues after removal processing in Example 1.

A polishing pad made of foamed urethane resin was attached to a polishing machine, after dressing of the polishing pad was performed by using a dresser with a surface covered with diamonds, dummy polishing was performed five times in a row under conditions (the following dummy polishing conditions): a polishing load of 200 g/cm$^2$ and a polishing stock removal of 15 µm, and the amount of polishing residues was measured every time 15-µm dummy polishing was performed. After the dummy polishing and the measurement of the amount of polishing residues were repeated five times, dressing of the polishing pad was performed by using a dresser with a surface covered with diamonds and cleaning was performed by spraying high-pressure jet water on the polishing pad, as processing to remove the polishing residues. Then, the amount of polishing residues after the removal processing was measured. The amount of polishing residue measured every time 15-µm dummy polishing was performed and the amount of polishing residues after the removal processing are shown in FIG. 3.

(Dummy Polishing Conditions)

Polishing machine used: a 30B double-side polishing machine

Sample wafer: CZ, P-type, crystal orientation <100>, a diameter of 300 mm, a silicon wafer Polishing pad: a polishing pad made of foamed urethane resin Polishing agent: a colloidal silica polishing agent Polishing load: 200 g/cm$^2$ Polishing stock removal: 15 µm As a result of a comparison between the amount of polishing residues after the removal processing which was measured in Example 1 described above and the reference value which was determined in advance in Comparative Example 1 described above, since the amount of polishing residues after the removal processing was greater than or equal to the reference value, the polishing pad of Example 1 was judged to have risen and selected as a polishing pad to be used in main polishing, which will be described later.

Figure 5:
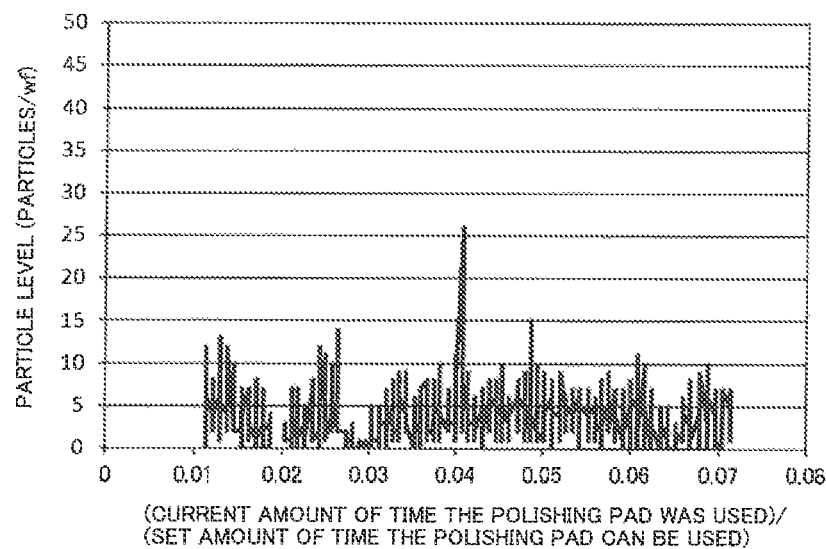
FIG. 5 is a graph showing the particle level in each amount of time the polishing pad was used in Example 1.

Next, polishing (main polishing) of a wafer was performed under the main polishing conditions similar to those of Comparative Example 1 by using the selected polishing pad, and the amount of polishing residues and the particle level in each amount of time the polishing pad was used were measured. The amount of polishing residues in each amount of time the polishing pad was used is shown in FIG. 4. Moreover, the particle level in each amount of time the polishing pad was used is shown in FIG. 5.

As shown in FIG. 4, the amount of polishing residues at a point in time at which the value of (the current amount of time the polishing pad was used)/(the set amount of time the polishing pad can be used) was 0 in Example 1, was equal to the amount of polishing residues at a point in time at which the value of (the current amount of time the polishing pad was used)/(the set amount of time the polishing pad can be used) was 0.05 in Comparative Example 1. That is, the polishing pad of Example 1 has sufficiently risen to the same degree as that at a point in time at which the value of (the current amount of time the polishing pad was used)/(the set amount of time the polishing pad can be used) is 0.05 in Comparative Example 1.

As shown in FIG. 6, in Comparative Example 1 in which the main polishing was performed by using the polishing pad whose rise was insufficient, the number of particles was large between a point in time at which the value of (the current amount of time the polishing pad was used)/(the set amount of time the polishing pad can be used) was 0 and a point in time at which the value was 0.05 and gradually decreases at and after a point in time at which the value was 0.05. By contrast, as shown in FIG. 5, in Example 1 in which the main polishing was performed by using the polishing pad which had sufficiently risen, the particle level observed between a point in time at which the value of (the current amount of time the polishing pad was used)/(the set amount of time the polishing pad can be used) was 0 and a point in time at which the value was 0.05 was improved.

The above results reveal that the method for raising a polishing pad and the polishing method of the present invention can improve the particle level in the polishing pad life early stage. Moreover, since it is possible to judge a rise of a polishing pad by a definite criterion: the amount of polishing residues, it is possible to prevent a waste of time or costs from being caused by dummy polishing or the like which is performed more than necessary.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A method for raising a polishing pad for polishing a silicon wafer, wherein
   a polishing pad made of foamed urethane resin is attached to a polishing machine,
   after dressing is performed, dummy polishing is performed,
   after processing to remove polishing residues that have built up in the polishing pad by the dummy polishing is then performed, an amount of polishing residues in the polishing pad is measured, and
   a rise of the polishing pad subjected to the dummy polishing is judged based on the measured amount of polishing residues, and wherein
   the judgment is made as follows:
      by performing polishing of a silicon wafer by using a reference polishing pad made of foamed urethane resin separately subjected only to dressing, processing to remove polishing residues which is performed by the same means as that used in the removal processing after the dummy polishing, and measurement of an amount of polishing residues after the removal processing, the amount of polishing residues in the reference polishing pad at a point in time at which a value of, i.e., an amount of time the reference polishing pad was used÷a previously set life of the reference polishing pad, is 0.05 is determined as a reference value in advance, and,
      if the amount of polishing residues measured after the dummy polishing and the removal processing is greater than or equal to the reference value, a judgment is made that the polishing pad subjected to the dummy polishing has risen.

2. The method for raising a polishing pad according to claim 1, wherein
   the amount of polishing residues is measured by detecting a signal containing a Si—K$\alpha$ ray from a fluorescent X-ray spectrum which is obtained by a fluorescent X-ray analysis method.

3. The method for raising a polishing pad according to claim 2, wherein
   the processing to remove polishing residues is performed by dressing and high-pressure jet water cleaning.

4. The method for raising a polishing pad according to claim 1, wherein
   the processing to remove polishing residues is performed by dressing and high-pressure jet water cleaning.

5. The method for raising a polishing pad according to claim 1, wherein
   the polishing machine is a double-side polishing machine.

6. A method for polishing a silicon wafer by using a polishing pad, wherein
   a polishing pad made of foamed urethane resin is attached to a polishing machine,
   after dressing is performed, dummy polishing is performed,
   after processing to remove polishing residues that have built up in the polishing pad by the dummy polishing is then performed, an amount of polishing residues in the polishing pad is measured,
   a polishing pad that is used in polishing of the silicon wafer is selected based on the measured amount of polishing residues, and
   polishing of the silicon wafer is performed by using the selected polishing pad, and wherein
   the selection is made as follows:
      by performing polishing of a silicon wafer by using a reference polishing pad made of foamed urethane resin separately subjected only to dressing, processing to remove polishing residues which is performed by the same means as that used in the removal processing after the dummy polishing, and measurement of an amount of polishing residues after the removal processing, the amount of polishing residues in the reference polishing pad at a point in time at which a value of, i.e., an amount of time the reference polishing pad was used÷a previously set life of the reference polishing pad, is 0.05 is determined as a reference value in advance, and
      a polishing pad whose amount of polishing residues measured after the dummy polishing and the removal processing is greater than or equal to the reference value is selected as a polishing pad that is used in polishing of the silicon wafer.

7. The polishing method according to claim 6, wherein the amount of polishing residues is measured by detecting a signal containing a Si—Kα ray from a fluorescent X-ray spectrum which is obtained by a fluorescent X-ray analysis method.

8. The polishing method according to claim 7, wherein the processing to remove polishing residues is performed by dressing and high-pressure jet water cleaning.

9. The polishing method according to claim 6, wherein the processing to remove polishing residues is performed by dressing and high-pressure jet water cleaning.

10. The polishing method according to claim 6, wherein the polishing machine is a double-side polishing machine.

* * * * *